(12) United States Patent
Hwang et al.

(10) Patent No.: US 9,068,166 B2
(45) Date of Patent: Jun. 30, 2015

(54) USE OF COMPOUNDS FOR INDUCING DIFFERENTIATION OF MESENCHYMAL STEM CELLS TO CHONDROCYTES

(75) Inventors: Ki Chul Hwang, Seoul (KR); Yang Soo Jang, Seoul (KR); Gyoon Hee Han, Gyeonggi-do (KR)

(73) Assignee: Industry-Academic Cooperation Foundation Yonsei University, Seoul (KR)

( * ) Notice: Subject to any disclaimer, the term of this patent is extended or adjusted under 35 U.S.C. 154(b) by 4 days.

(21) Appl. No.: 13/823,653

(22) PCT Filed: Sep. 16, 2011

(86) PCT No.: PCT/KR2011/006867
§ 371 (c)(1),
(2), (4) Date: Mar. 14, 2013

(87) PCT Pub. No.: WO2012/036512
PCT Pub. Date: Mar. 22, 2012

(65) Prior Publication Data
US 2013/0236969 A1   Sep. 12, 2013

(30) Foreign Application Priority Data
Sep. 16, 2010  (KR) .................... 10-2010-0091081

(51) Int. Cl.
*C07C 311/21* (2006.01)
*C07D 215/36* (2006.01)
(Continued)

(52) U.S. Cl.
CPC .............. *C12N 5/0655* (2013.01); *A61K 31/18* (2013.01); *A61K 31/47* (2013.01); *C12N 2501/999* (2013.01); *C12N 2501/727* (2013.01); *C07C 311/21* (2013.01); *C07D 215/36* (2013.01); *C07C 311/17* (2013.01); *C07C 311/20* (2013.01); *C07C 2101/14* (2013.01); *C12N 2506/1353* (2013.01)

(58) Field of Classification Search
None
See application file for complete search history.

(56) References Cited

U.S. PATENT DOCUMENTS 4,273,844 A   6/1981   Kobayashi et al.
5,216,150 A   6/1993   Hidaka et al.
(Continued)

FOREIGN PATENT DOCUMENTS

EP          1402890         3/2004
KR   10-2003-0094384       12/2003
(Continued)

OTHER PUBLICATIONS

International Search Report for PCT/KR2011/006867 mailed Apr. 4, 2012, 3 pages.
(Continued)

*Primary Examiner* — Blaine Lankford
*Assistant Examiner* — Trent Clarke
(74) *Attorney, Agent, or Firm* — Swanson & Bratschun, L.L.C.

(57) ABSTRACT

Use of a compound of Formula 1 for inducing differentiation of mesenchymal stem cells to chondrocytes, and a pharmaceutical composition for treating a cartilage disease, which includes chondrocytes in which differentiation from mesenchymal stem cells is induced by the compound of Formula 1, are provided. Differentiation of the mesenchymal stem cells treated with the compound of Formula 1 to chondrocytes is specifically induced, and thus the compound can be used to effectively treat a cartilage disease such as arthritis, cartilage damage, and a cartilage defect.

4 Claims, 3 Drawing Sheets

(51) Int. Cl.
   *C12N 5/071*    (2010.01)
   *C12N 5/077*    (2010.01)
   *A61K 31/18*    (2006.01)
   *A61K 31/47*    (2006.01)
   *C07C 311/17*   (2006.01)
   *C07C 311/20*   (2006.01)

(56) References Cited

U.S. PATENT DOCUMENTS 6,440,966 B1    8/2002    Barrett et al.
2003/0104970 A1*  6/2003  Wang ............................... 514/1

FOREIGN PATENT DOCUMENTS

| WO | WO 2005/011697 | A2 | 2/2005 |
| WO | WO 2005/011697 | A3 | 2/2005 |
| WO | WO 2008/089351 |    | 7/2008 |
| WO | WO 2009/116840 | A2 | 9/2009 |
| WO | WO 2009/116840 | A3 | 9/2009 |
| WO | WO 2009116840 | A2 * | 9/2009 |
| WO | WO 2012/129562 | A2 | 9/2012 |
| WO | WO 2012/129562 | A3 | 9/2012 |

OTHER PUBLICATIONS

Allsopp et al. (2010) MedChemComm 1 p. 16-29 "Small molecule modulation of stem cells in regenerative medicine: recent applications and future direction".

Extended European Search Report, Feb. 5, 2014, for EP 11825472.1, 15 pages.

Hwang et al. (2008) *PNAS* 105:21 p. 7467-7471 "Chemicals that modulate stem cell differentiation".

* cited by examiner

USE OF COMPOUNDS FOR INDUCING DIFFERENTIATION OF MESENCHYMAL STEM CELLS TO CHONDROCYTES

RELATED APPLICATIONS

This application is a 35 U.S.C. §371 national phase application of PCT/KR2011/006867 (WO2012/036512), filed on Sep. 16, 2011, entitled "Use of a Compound for Inducing Differentiation of Mesenchymal Stem Cells into Cartilage Cells", which application claims the benefit of Korean Patent Application No. 10-2010-0091081, filed Sep. 16, 2010, which is incorporated herein by reference in its entirety.

TECHNICAL FIELD

The present invention relates to use of a compound represented by Formula 1 for inducing differentiation of mesenchymal stem cells to chondrocytes, and a pharmaceutical composition for treating a cartilage disease, which includes chondrocytes in which differentiation from mesenchymal stem cells is induced by the compound of Formula 1.

Incorporated by reference herein in its entirety is the Sequence Listing entitled "PCTKR2011006867Sequence_Listing_ST25," created Apr. 1, 2013, size of 3 kilobytes.

BACKGROUND ART

In recent years, drugs such as pain-killing drugs, steroid formulations, or non-steroid anti-inflammatory drugs are generally used to treat a cartilage disease such as arthritis, and auxiliary materials such as hyaluronic acid, glucosamine, or chondroitin is also used to protect cartilage. However, the above-described drugs serves to non-specifically relieve pain or an inflammatory response, but do not induce regeneration or proliferation of chondrocytes. Also, a chondroprotective agent such as hyaluronic acid aids in maintaining tissues of a cartilage, but does not have an effect on regeneration or proliferation of the chondrocytes.

Therefore, there have been recent attempts to develop a method of replacing damaged cartilage tissue using cell therapy and a tissue engineering technique so as to regenerate the damaged cartilage tissue, for instance, in degenerative arthritis. However, while the cell therapy and tissue engineering requires a large amount of chondrocytes, it is not easy to obtain the chondrocytes in a large amount due to the de-differentiation of the chondrocytes, that is, disappearance of characteristics of the chondrocytes during ex vivo proliferation of the chondrocytes.

DISCLOSURE

Technical Problem

The present invention is directed to providing a method of inducing differentiation of mesenchymal stem cells to chondrocytes for application of mesenchymal stem cells as a cellular therapeutic agent for treating a cartilage disease.

Technical Solution

When lower heterogeneity between transplanted cells and a host tissue is achieved, an engraftment rate of the transplanted cells may be enhanced. In consideration of this fact, the present inventors have conducted continuous research on a method of inducing differentiation of mesenchymal stem cells to chondrocytes. As a result, they have found that a compound represented by the following Formula 1 can induce differentiation of mesenchymal stem cells to chondrocytes.

The following exemplary embodiments disclose that human adipose tissue-derived mesenchymal stem cells modified ex vivo by the compound of Formula 1 are differentiated to chondrocytes, and a marker relating the differentiation to the chondrocytes is expressed.

Therefore, one aspect of the present invention provides use of a compound of Formula 1 for inducing differentiation of mesenchymal stem cells to chondrocytes, a method of inducing differentiation of mesenchymal stem cells to chondrocytes, which comprises treating the compound of Formula 1 with the mesenchymal stem cells, and a composition for inducing differentiation of mesenchymal stem cells to chondrocytes, which comprises the compound of Formula 1.

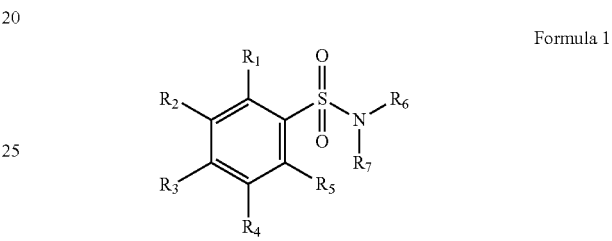

Formula 1

In Formula 1, $R_1$ to $R_3$ are each independently hydrogen, $C_{6-12}$ aryl, $C_{1-12}$ alkyl, $C_{1-12}$ alkoxy, hydroxyl, carboxyl, or halogen, or $R_1$ and $R_2$ or $R_2$ and $R_3$ are joined together to form an aryl or heteroaryl ring having 5 to 12 carbon atoms, $R_4$ and $R_5$ are each independently hydrogen, $C_{1-12}$ alkyl, $C_{1-12}$ alkoxy, hydroxyl, carboxyl, or halogen, $R_6$ is $C_{6-12}$ aryl, $C_{3-12}$ cycloalkyl, or $C_{1-4}$ alkyl substituted with $C_{6-12}$ aryl, $R_7$ is hydrogen or $C_{1-4}$ alkyl, and $R_1$ to $R_6$ are each independently unsubstituted, or further substituted with at least one substituent selected from the group consisting of $C_{1-4}$ alkyl, hydroxyl, hydroxyl $C_{1-4}$ alkyl, nitro, carboxyl, and halogen.

Here, the "substituted" group is formed by replacing at least one hydrogen atom with at least one non-hydrogen group, or has to satisfy the valence requirements and be formed by substitution of a chemically stable compound. Unless explicitly defined to be "unsubstituted" in this specification, it should be understood that all substituents may be substituted or unsubstituted. For example, each of the substituents $R_1$ to $R_6$ may be substituted again with one of the above-described substituents.

The term "alkyl" generally refers to a linear and branched saturated hydrocarbon group having the given number of carbon atoms (for example, 1 to 12 carbon atoms). Examples of the alkyl group include, but are not limited to, methyl, ethyl, n-propyl, i-propyl, n-butyl, s-butyl, i-butyl, t-butyl, pent-1-yl, pent-2-yl, pent-3-yl, 3-methylbut-1-yl, 3-methylbut-2-yl, 2-methylbut-2-yl, 2,2,2-trimethyleth-1-yl, n-hexyl, n-heptyl, and n-octyl.

The term "alkoxy" refers to an alkyl-O—. Here, the alkyl is as defined above. Examples of the alkoxy group include, but are not limited to, methoxy, ethoxy, n-propoxy, i-propoxy, n-butoxy, s-butoxy, t-butoxy, n-pentoxy, and s-pentoxy. The alkoxy may be attached to a substrate or a parent group in a cyclic atom as long as the attachment does not violate the valence requirements. Similarly, the alkoxy group may include at least one non-hydrogen substituent as long as the attachment does not violate the valence requirements.

The term "carboxyl" refers to a divalent radical, —C(O)OH, and the term "nitro" refers to N(O)$_2$. In this specification, (O) means that an oxygen atom is bound to an atom such as carbon, nitrogen or sulfur by means of a double bond.

The term "aryl" refers to a monovalent or divalent aromatic group containing a 5- or 6-membered monocyclic aromatic group having 0 to 4 heteroatoms independently selected from nitrogen, oxygen and sulfur. When the aryl contains at least one heteroatom, the aryl is also referred to as a "heteroaryl." Examples of the monocyclic aryl group include, but are not limited to, phenyl, pyrrolyl, furanyl, thiophenyl, thiazolyl, isothiazolyl, imidazolyl, triazolyl, tetrazolyl, pyrazolyl, oxazolyl, isooxazolyl, pyridinyl, pyrazinyl, pyridazinyl, and pyrimidinyl. Also, the aryl group includes a dicyclic or tricyclic group containing the fused 5- or 6-membered ring as described above. Examples of the polycyclic aryl group include, but are not limited to, naphthyl, biphenyl, anthracenyl, pyrenyl, carbazolyl, benzoxazolyl, benzodioxazolyl, benzothiazolyl, benzoimidazolyl, benzothiophenyl, quinolinyl, isoquinolinyl, indolyl, benzofuranyl, purinyl, and indolizinyl. The aryl group may be attached to a substrate or a parent group in a cyclic atom as long as the attachment does not violate the valence requirements. Similarly, the aryl group may include at least one non-hydrogen substituent as long as the attachment does not violate the valence requirements.

According to one exemplary embodiment, $R_1$ to $R_3$ are each independently hydrogen, phenyl, $C_{1-4}$ alkyl, or halogen, or $R_1$ and $R_2$ or $R_2$ and $R_3$ are joined together to form a pyridine or benzene ring, $R_4$ and $R_5$ are each independently hydrogen, $C_{1-4}$ alkyl, or halogen, $R_6$ is phenyl, naphthalyl, $C_{3-12}$ cycloalkyl, or $C_{1-4}$ alkyl substituted with phenyl, $R_7$ is hydrogen or $C_{1-4}$ alkyl, and $R_1$ to $R_6$ may each be independently unsubstituted, or further substituted with at least one substituent selected from the group consisting of $C_{1-4}$ alkyl, hydroxyl, hydroxyl $C_{1-4}$ alkyl, nitro, carboxyl, and halogen.

According to another exemplary embodiment, $R_1$ and $R_2$ are each independently hydrogen, or are joined together to form a pyridine ring, $R_3$ is hydrogen, phenyl, or $C_{1-4}$ alkyl, or is joined together with $R_2$ to form a benzene ring, $R_4$ and $R_5$ are each independently hydrogen, $R_6$ is phenyl, naphthalyl, $C_{5-10}$ cycloalkyl, or $C_{1-4}$ alkyl substituted with phenyl, $R_7$ is hydrogen or $C_{1-4}$ alkyl, and $R_1$ to $R_6$ may each be independently unsubstituted, or further substituted with at least one substituent selected from the group consisting of $C_{1-4}$ alkyl, hydroxyl, hydroxyl $C_{1-4}$ alkyl, nitro, carboxyl, and halogen.

According to still another exemplary embodiment, the compound of Formula 1 may be at least one compound selected from the group consisting of:

1) quinoline-8-sulfonic acid (4-hydroxy-phenyl)-amide;
2) quinoline-8-sulfonic acid (7-hydroxy-naphthalen-1-yl)-amide;
3) 2-hydroxy-5-(quinoline-8-sulfonylamino)-benzoic acid;
4) 5-(4-tert-butyl-benzenesulfonylamino)-2-hydroxy-benzoic acid;
5) biphenyl-4-sulfonic acid (5-hydroxy-naphthalen-1-yl)-amide;
6) N-(4-hydroxy-naphthalen-1-yl)-4-methyl-benzenesulfonamide;
7) naphthalene-2-sulfonic acid (4-hydroxyl-phenyl)-amide;
8) N-(5-hydroxyl-naphthalen-1-yl)-4-methyl-benzenesulfonamide;
9) N-(7-hydroxyl-naphthalen-1-yl)-4-methyl-benzenesulfonamide;
10) 4-tert-butyl-N-(3-hydroxyl-phenyl)-benzenesulfonamide;
11) 4-tert-butyl-N-(2-chloro-4-hydroxyl-phenyl)-benzenesulfonamide;
12) biphenyl-4-sulfonic acid (2-chloro-4-hydroxyl-phenyl)-amide;
13) naphthalene-2-sulfonic acid (2-chloro-4-hydroxyl-phenyl)-amide;
14) 4-tert-butyl-N-(2-fluoro-4-hydroxyl-phenyl)-benzenesulfonamide;
15) biphenyl-4-sulfonic acid (2-fluoro-4-hydroxyl-phenyl)-amide;
16) naphthalene-2-sulfonic acid (2-fluoro-4-hydroxyl-phenyl)-amide;
17) 4-tert-butyl-N-(3-fluoro-4-hydroxyl-phenyl)-benzenesulfonamide;
18) biphenyl-4-sulfonic acid (3-fluoro-4-hydroxyl-phenyl)-amide;
19) naphthalene-2-sulfonic acid (3-fluoro-4-hydroxyl-phenyl)-amide;
20) naphthalene-2-sulfonic acid (3-nitro-4-hydroxyl-phenyl)-amide;
21) 4-tert-butyl-N-[2-(3,4-dihydroxyl-phenyl)-ethyl]-benzenesulfonamide;
22) biphenyl-4-sulfonic acid [2-(3,4-dihydroxyl-phenyl)-ethyl]-amide;
23) naphthalene-2-sulfonic acid [2-(3,4-dihydroxyl-phenyl)-ethyl]amide;
24) 4-tert-butyl-N-ethyl-N-(5-hydroxyl-2-methyl-phenyl)-benzenesulfonamide;
25) naphthalene-2-sulfonic acid ethyl-(5-hydroxyl-2-methyl-phenyl)-amide;
26) 4-tert-butyl-N-[4-(2-hydroxyl-ethyl)-cyclohexyl]-benzenesulfonamide;
27) biphenyl-4-sulfonic acid [4-(2-hydroxyl-ethyl)-cyclohexyl]-amide; and
28) naphthalene-2-sulfonic acid [4-(2-hydroxyl-ethyl)-cyclohexyl]-amide.

In the present invention, the kind of mesenchymal stem cells used to induce differentiation to chondrocytes is not particularly limited, and thus the mesenchymal stem cells used in the present invention may also be used regardless of what the mesenchymal stem cells are derived from.

The mesenchymal stem cells may be obtained from a known mesenchymal stem cell source, for example, bone marrow, tissue, an embryo, cord blood, blood, or body fluid. An animal that is a target subject whose bone marrow, tissue, etc. is to be extracted may be a mammal. When the animal is a human being, the bone marrow, the tissue, etc. may be derived from a patient whose mesenchymal stem cells differentiation-induced to chondrocytes by treatment with the composition according to the present invention are administered as a cellular therapeutic agent, or derived from a human being other than the patient. Such a method of obtaining mesenchymal stem cells from the known mesenchymal stem cell source is widely known in the related art.

Meanwhile, a method of treating the mesenchymal stem cells with the compound of Formula 1 is not particularly limited, but any in which the compound of Formula 1 is brought into contact with the mesenchymal stem cells for a given period of time to induce differentiation of the mesenchymal stem cells to chondrocytes may be used. According to one exemplary embodiment, treatment with the compound of Formula 1 may be performed by incubating the mesenchymal stem cells in a medium comprising the compound of Formula 1.

A concentration of the compound of Formula 1 with which the mesenchymal stem cells are treated may vary according to the specific kind of the compound of Formula 1, the treatment duration of the mesenchymal stem cells, or a level of differentiation to chondrocytes. According to one exemplary embodiment, the compound Formula 1 may be used at a concentration of 0.01 to 100 µM.

In consideration of a time generally required to induce differentiation of the mesenchymal stem cells, the mesenchymal stem cells may be incubated for 5 to 15 days in a medium comprising the compound of Formula 1, but the present invention is not limited thereto. A duration required to treat the mesenchymal stem cells with the compound of Formula 1 may vary according to the kind or concentration of the compound of Formula 1 to be treated.

In the present invention, the term "chondrocytes" include all kinds of cells covering from the mesenchymal stem cells to chondrocytes whose differentiation is induced or cells whose differentiation to chondrocytes is under way. In the present invention, the chondrocytes that are differentiation-induced from the mesenchymal stem cells by treatment with the compound of Formula 1 express specific marker associated with chondrogenesis. In the chondrocytes obtained according to the method of the present invention, an expression level of such a specific marker may be increased compared to that of the mesenchymal stem cells. The specific marker may be selected from the group consisting of fibronectin, β1-integrin, α5-integrin and N-cadherin, but the present invention is not limited thereto.

Another aspect of the present invention provides a composition for inducing differentiation of mesenchymal stem cells to chondrocytes, which comprises the compound of Formula 1. One exemplary embodiment of the compound of Formula 1 is as described above. The composition may comprise a medium widely used to incubate the mesenchymal stem cells. For example, such a medium may include a minimum essential medium alpha (MEM-alpha), a mesenchymal stem cell growth medium (MSCGM), and a Dulbecco's modified eagle's medium (DMEM), but the present invention is not limited thereto. Also, the composition for inducing differentiation of mesenchymal stem cells to chondrocytes, which comprises the compound of Formula 1, may be introduced into a human body, regardless of the mesenchymal stem cells. That is, the composition comprising the compound of Formula 1 may be separately administered before/after administration of the mesenchymal stem cells or administered simultaneously with administration of the mesenchymal stem cells. In this case, the composition may comprise a known pharmaceutical carrier suitable for administration of the compound of Formula 1.

Still another aspect of the present invention provides a pharmaceutical composition for treating a cartilage disease, which comprises the chondrocytes in which differentiation from mesenchymal stem cells is induced using the method. Such a pharmaceutical composition for treating a cartilage disease may be effectively used to treat a cartilage disease such as arthritis, cartilage damage or a cartilage defect, but the present invention is not limited thereto. The pharmaceutical composition may further comprise a known carrier used in the related art to transplant stem cells. Also, an effective amount of the chondrocytes may be in a range of $1 \times 10^4$ to $1 \times 10^8$ cells/kg. However, the effective amount of the chondrocytes may be optionally increased or decreased according to the weight, age and sex of a patient, or a severity of a lesion. The formulation according to the present invention may be applied to a human body by parenteral or local administration. For this purpose, an effective component may be suspended or dissolved in a pharmaceutically acceptable carrier according to a conventional method. In this case, a water-soluble carrier may be used as the pharmaceutically acceptable carrier.

Still another aspect of the present invention provides a compound represented by the following Formula 1, and a method of preparing the same.

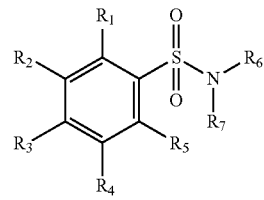

Formula 1

In Formula 1, $R_1$ to $R_3$ are each independently hydrogen, $C_{6-12}$ aryl, $C_{1-12}$ alkyl, $C_{1-12}$ alkoxy, hydroxyl, carboxyl, or halogen, or $R_1$ and $R_2$ or $R_2$ and $R_3$ are joined together to form an aryl or heteroaryl ring having 5 to 12 carbon atoms, $R_4$ and $R_5$ are each independently hydrogen, $C_{1-12}$ alkyl, $C_{1-12}$ alkoxy, hydroxyl, carboxyl, or halogen, $R_6$ is $C_{6-12}$ aryl, $C_{3-12}$ cycloalkyl, or $C_{1-4}$ alkyl substituted with $C_{6-12}$ aryl, $R_7$ is hydrogen or $C_{1-4}$ alkyl, and $R_1$ to $R_6$ may each be independently unsubstituted, or further substituted with at least one substituent selected from the group consisting of $C_{1-4}$ alkyl, hydroxyl, hydroxyl $C_{1-4}$ alkyl, nitro, carboxyl, and halogen.

One exemplary embodiment of the compound of Formula 1 is as described above.

According to one exemplary embodiment, the compound of Formula 1 may be prepared as shown in the following Scheme 1.

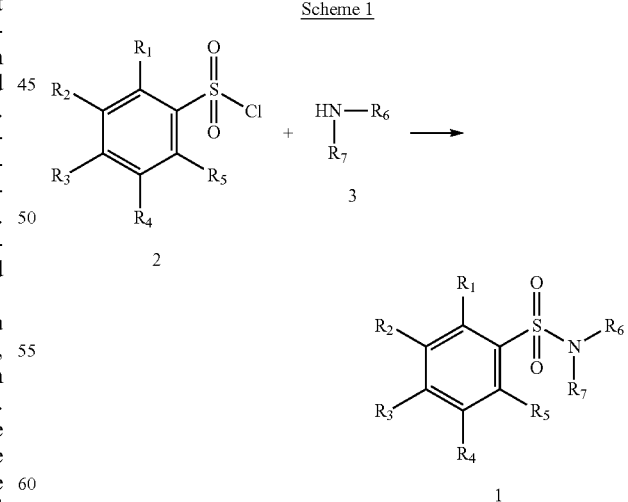

In Scheme 1, $R_1$ to $R_7$ are as defined above.

Yet another aspect of the present invention provides a method of preparing a compound of Formula 1, which comprises reacting the compound of Formula 2 with the compound of Formula 3 to prepare the compound of Formula 1.

Referring to one example of the method of preparing a compound of Formula 1 according to the present invention, the compound of Formula 1 may be obtained by introducing the compound of Formula 3 and triethylamine into a 0.2 M tetrahydrofuran solution including the compound of Formula 2 while stirring, reacting the resulting mixture for 12 hours, filtering the mixture with ethylacetate, concentrating the filtered mixture under a reduced pressure, and purifying the obtained primary compound using a method such as silica gel column chromatography.

Advantageous Effects

The mesenchymal stem cells treated with the compound of Formula 1 can be specifically differentiation-induced to chondrocytes, and thus the compound can be used to effectively treat a cartilage disease such as arthritis, cartilage damage, and a cartilage defect.

BEST MODE

Figure 1:
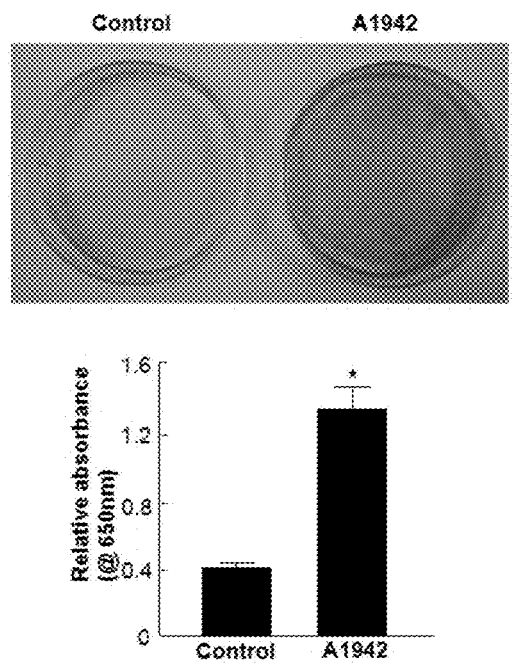
FIG. 1 shows the Alcian Blue dyeing results indicating that a compound of Formula 1 induces differentiation of mesenchymal stem cells to chondrocytes.

The advantages and features of the present invention and the method of revealing them will be explicit from the following examples described in detail. However, it is to be distinctly understood that the present invention is not limited thereto but may be otherwise variously embodied and practiced. It is obvious that the following examples are to complete the disclosure of the invention and to indicate the scope of the present invention to a skilled artisan completely, and the present invention will be defined only by the scope of the claims.

EXAMPLES

Example

Synthesis of Compound of Formula 1

Example 1

Preparation of (quinoline-8-sulfonic acid (4-hydroxy-phenyl)-amide

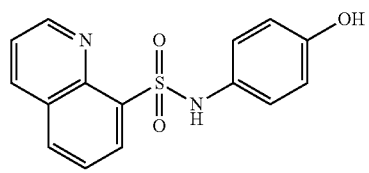 [SMILES: O=S(=O)(Nc1ccc(O)cc1)c1cccc2cccnc12]

The compound of Formula 3 (216 mg, 1.98 mmol) and triethylamine (550 ml, 3.96 mmol) were introduced into a 0.2 M tetrahydrofuran solution including the compound of Formula 2 (300 mg, 1.32 mmol) while stirring, and stirred for 12 hours. The resulting mixture was filtered with ethylacetate, and then concentrated under a reduced pressure. The obtained primary compound was purified using silica gel column chromatography (eluent: ethylacetate:methylene chloride:hexane=2:1:3) to obtain a title compound at a yield of 49% (194 mg).

$^1$H-NMR (500 MHz, DMSO-d6) δ 9.46 (s, 1H), 9.19 (s, 1H), 9.15 (dd, J=4.2, 1.8 Hz, 1H), 8.53 (dd, J=8.4, 1.7 Hz, 1H), 8.25 (dd, J=8.2, 1.4 Hz, 1H), 8.21 (dd, J=7.3, 1.4 Hz, 1H), 7.74 (dd, J=8.3, 4.2 Hz, 1H), 7.68-7.63 (m, 1H), 6.75-6.70 (m, 2H), 6.53-6.41 (m, 2H)

Examples 2 to 28

Compounds of Examples 2 to 28 were prepared in the same manner as in the preparation method described in Example 1. Chemical structures and physical properties of the prepared compounds are listed in the following Table 1 and Table 2.

TABLE 1

| Examples | Compound Number | Chemical Structure | Formula | IUPAC Nomenclature |
| --- | --- | --- | --- | --- |
| 1 | A1942 | 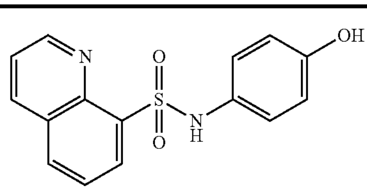 | C15H12N2O3S | Quinoline-8-sulfonic acid (4-hydroxy-phenyl)-amide |

TABLE 1-continued

| Examples | Compound Number | Chemical Structure | Formula | IUPAC Nomenclature |
|---|---|---|---|---|
| 2 | A1943 | 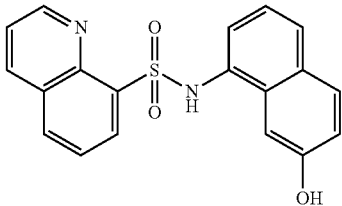 [SMILES: O=S(=O)(Nc1cccc2ccc(O)cc12)c1cccc2cccnc12] | C19H14N2O3S | Quinoline-8-sulfonic acid (7-hydroxy-naphthalen-1-yl)-amide |
| 3 | A1944 | 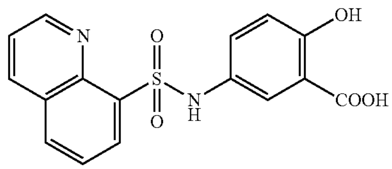 [SMILES: O=C(O)c1cc(NS(=O)(=O)c2cccc3cccnc23)ccc1O] | C16H12N2O5S | 2-Hydroxy-5-(quinoline-8-sulfonylamino)-benzoic acid |
| 4 | A1948 | 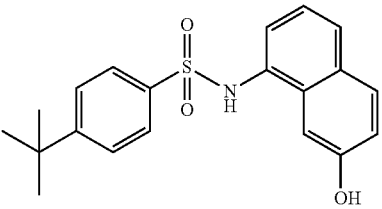 [SMILES: CC(C)(C)c1ccc(S(=O)(=O)Nc2cccc3ccc(O)cc23)cc1] | C17H19NO5S | 5-(4-Tert-butyl-benzenesulfonyl-amino)-2-hydroxy-benzoic acid |
| 5 | A1949 | 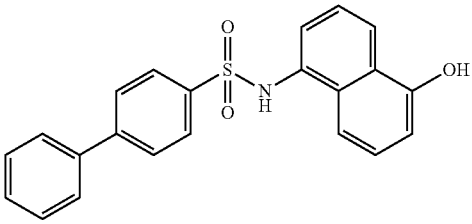 [SMILES: O=S(=O)(Nc1cccc2c(O)cccc12)c1ccc(-c2ccccc2)cc1] | C22H17NO3S | Biphenyl-4-sulfonic acid (5-hydroxy-naphthalen-1-yl)-amide |
| 6 | A1950 | 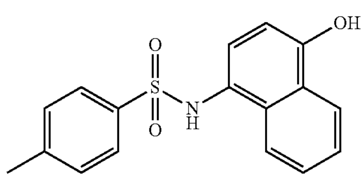 [SMILES: Cc1ccc(S(=O)(=O)Nc2ccc(O)c3ccccc23)cc1] | C17H15NO3S | N-(4-hydroxy-naphthalen-1-yl)-4-methyl-benzenesulfonamide |
| 7 | A1880 | 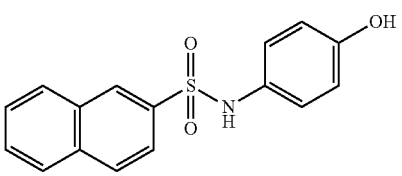 [SMILES: O=S(=O)(Nc1ccc(O)cc1)c1ccc2ccccc2c1] | C16H13NO3S | Naphthalene-2-sulfonic acid (4-hydroxyl-phenyl)-amide |
| 8 | A1881 | 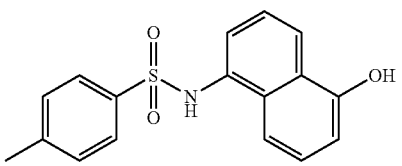 [SMILES: Cc1ccc(S(=O)(=O)Nc2cccc3c(O)cccc23)cc1] | C17H15NO3S | N-(5-hydroxyl-naphthalen-1-yl)-4-methyl-benzenesulfonamide |

TABLE 1-continued

| Examples | Compound Number | Chemical Structure | Formula | IUPAC Nomenclature |
|---|---|---|---|---|
| 9 | A1882 | 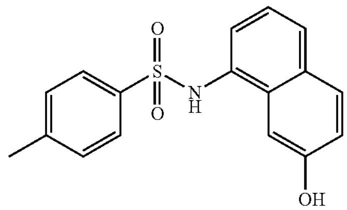 [SMILES: Cc1ccc(S(=O)(=O)Nc2cccc3ccc(O)cc23)cc1] | C17H15NO3S | N-(7-hydroxyl-naphthalen-1-yl)-4-methyl-benzenesulfonamide |
| 10 | A1999 | 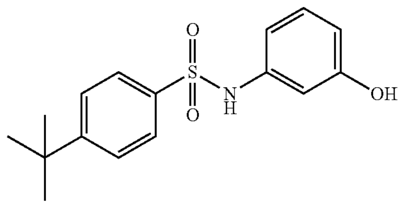 [SMILES: CC(C)(C)c1ccc(S(=O)(=O)Nc2cccc(O)c2)cc1] | C16H19NO3S | 4-tert-butyl-N-(3-hydroxyl-phenyl)-benzenesulfonamide |
| 11 | A2000 | 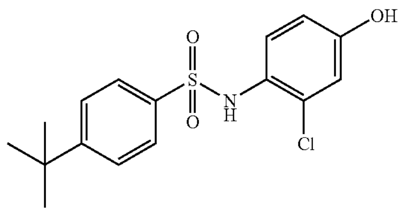 [SMILES: CC(C)(C)c1ccc(S(=O)(=O)Nc2ccc(O)cc2Cl)cc1] | C16H18ClNO3S | 4-tert-butyl-N-(2-chloro-4-hydroxyl-phenyl)-benzenesulfonamide |
| 12 | A2001 | 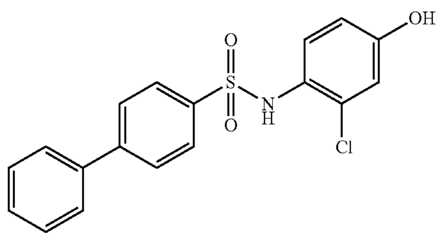 [SMILES: O=S(=O)(Nc1ccc(O)cc1Cl)c1ccc(-c2ccccc2)cc1] | C18H14ClNO3S | Biphenyl-4-sulfonic acid (2-chloro-4-hydroxyl-phenyl)-amide |
| 13 | A2002 | 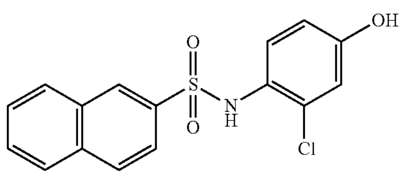 [SMILES: O=S(=O)(Nc1ccc(O)cc1Cl)c1ccc2ccccc2c1] | C16H12ClNO3S | Naphthalene-2-sulfonic acid (2-chloro-4-hydroxyl-phenyl)-amide |
| 14 | A2007 | 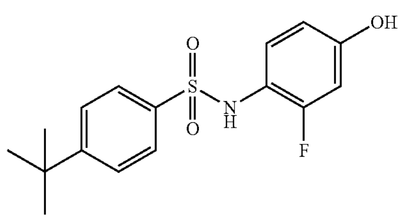 [SMILES: CC(C)(C)c1ccc(S(=O)(=O)Nc2ccc(O)cc2F)cc1] | C16H18FNO3S | 4-tert-butyl-N-(2-fluoro-4-hydroxyl-phenyl)-benzenesulfonamide |
| 15 | A2008 | 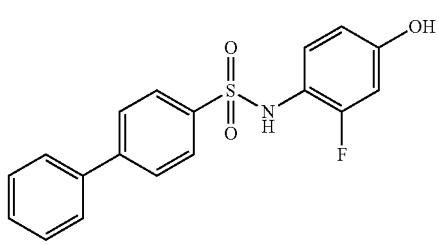 [SMILES: O=S(=O)(Nc1ccc(O)cc1F)c1ccc(-c2ccccc2)cc1] | C18H14FNO3S | Biphenyl-4-sulfonic acid (2-fluoro-4-hydroxyl-phenyl)-amide |

TABLE 1-continued

| Examples | Compound Number | Chemical Structure | Formula | IUPAC Nomenclature |
|---|---|---|---|---|
| 16 | A2009 | 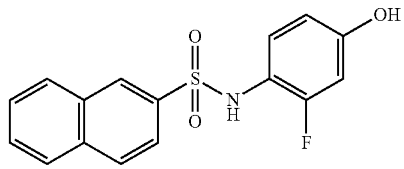 [SMILES: O=S(=O)(Nc1ccc(O)cc1F)c1ccc2ccccc2c1] | C16H12FNO3S | Naphthalene-2-sulfonic acid (2-fluoro-4-hydroxyl-phenyl)-amide |
| 17 | A2010 | 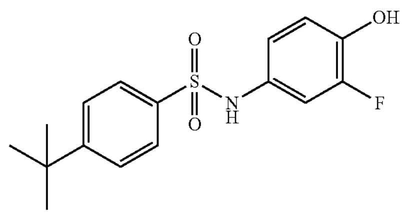 [SMILES: CC(C)(C)c1ccc(S(=O)(=O)Nc2ccc(O)c(F)c2)cc1] | C16H18FNO3S | 4-Tert-butyl-N-(3-fluoro-4-hydroxyl-phenyl)-benzenesulfonamide |
| 18 | A2011 | 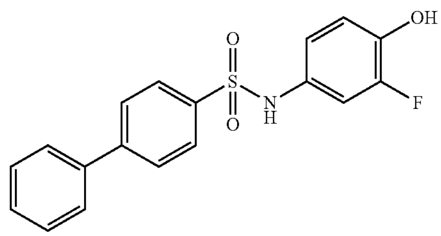 [SMILES: O=S(=O)(Nc1ccc(O)c(F)c1)c1ccc(-c2ccccc2)cc1] | C18H14FNO3S | Biphenyl-4-sulfonic acid (3-fluoro-4-hydroxyl-phenyl)-amide |
| 19 | A2012 | 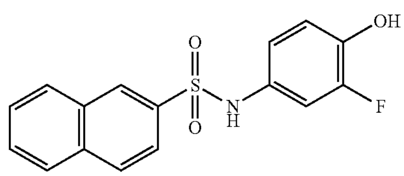 [SMILES: O=S(=O)(Nc1ccc(O)c(F)c1)c1ccc2ccccc2c1] | C16H12FNO3S | Naphthalene-2-sulfonic acid (3-fluoro-4-hydroxyl-phenyl)-amide |
| 20 | A2013 | 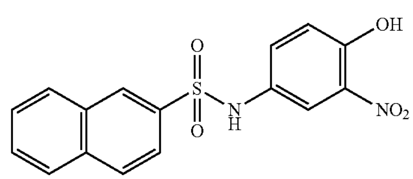 [SMILES: O=[N+]([O-])c1cc(NS(=O)(=O)c2ccc3ccccc3c2)ccc1O] | C16H12N2O5S | Naphthalene-2-sulfonic acid (3-nitro-4-hydroxyl-phenyl)-amide |
| 21 | A2062 | 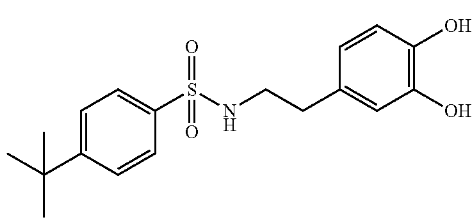 [SMILES: CC(C)(C)c1ccc(S(=O)(=O)NCCc2ccc(O)c(O)c2)cc1] | C18H23NO4S | 4-Tert-butyl-N-[2-(3,4-dihydroxyl-phenyl)-ethyl]-benzenesulfonamide |
| 22 | A2063 | 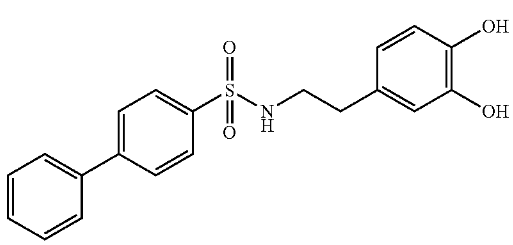 [SMILES: O=S(=O)(NCCc1ccc(O)c(O)c1)c1ccc(-c2ccccc2)cc1] | C20H19NO4S | Biphenyl-4-sulfonic acid [2-(3,4-dihydroxyl-phenyl)-ethyl]-amide |

TABLE 1-continued

| Examples | Compound Number | Chemical Structure | Formula | IUPAC Nomenclature |
|---|---|---|---|---|
| 23 | A2064 | 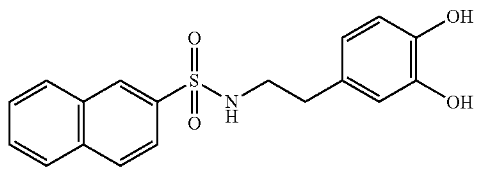 [SMILES: O=S(=O)(NCCc1ccc(O)c(O)c1)c1ccc2ccccc2c1] | C18H17NO4S | Naphthalene-2-sulfonic acid [2-(3,4-dihydroxyl-phenyl)-ethyl]-amide |
| 24 | A2065 | 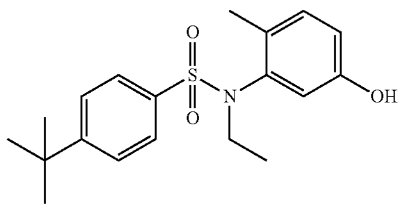 [SMILES: CCN(c1cc(O)ccc1C)S(=O)(=O)c1ccc(C(C)(C)C)cc1] | C19H25NO3S | 4-Tert-butyl-N-ethyl-N-(5-hydroxyl-2-methyl-phenyl)-benzenesulfonamide |
| 25 | A2066 | 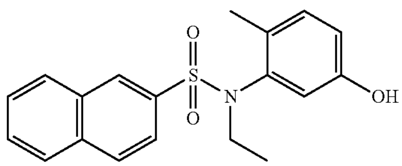 [SMILES: CCN(c1cc(O)ccc1C)S(=O)(=O)c1ccc2ccccc2c1] | C19H19NO3S | Naphthalene-2-sulfonic acid ethyl-(5-hydroxyl-2-methyl-phenyl)-amide |
| 26 | A2067 | 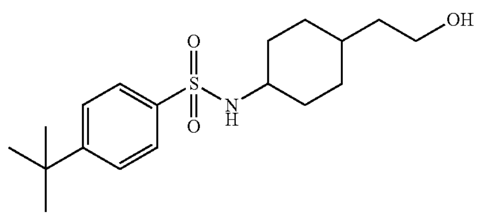 [SMILES: CC(C)(C)c1ccc(S(=O)(=O)NC2CCC(CCO)CC2)cc1] | C18H29NO3S | 4-Tert-butyl-N-[4-(2-hydroxyl-ethyl)-cyclohexyl]-benzenesulfonamide |
| 27 | A2068 | 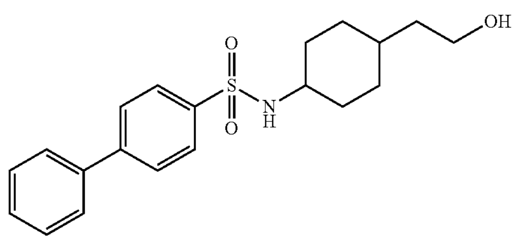 [SMILES: O=S(=O)(NC1CCC(CCO)CC1)c1ccc(-c2ccccc2)cc1] | C20H25NO3S | Biphenyl-4-sulfonic acid [4-(2-hydroxyl-ethyl)-cyclohexyl]-amide |
| 28 | A2069 | 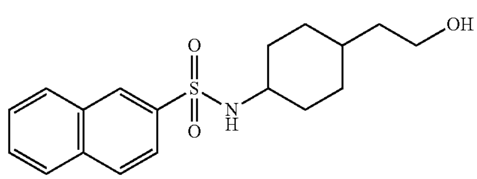 [SMILES: O=S(=O)(NC1CCC(CCO)CC1)c1ccc2ccccc2c1] | C18H23NO3S | Naphthalene-2-sulfonic acid [4-(2-hydroxyl-ethyl)-cyclohexyl]-amide |

TABLE 2

| Examples | Compound Number | MW | LCMS | NMR |
|---|---|---|---|---|
| 1 | A1942 | 300.34 | APCI (m/z) 301.05 (M$^+$) | $^1$H NMR (500 MHz, DMSO-d6) δ 9.46 (s, 1H), 9.19 (s, 1H), 9.15 (dd, J = 4.2, 1.8 Hz, 1H), 8.53 (dd, J = 8.4, 1.7 Hz, 1H), 8.25 (dd, J = 8.2, 1.4 Hz, 1H), 8.21 (dd, J = 7.3, 1.4 Hz, 1H), 7.74 (dd, J = 8.3, 4.2 Hz, 1H), 7.68-7.63 (m, 1H), 6.75-6.70 (m, 2H), 6.53-6.41 (m, 2H). |
| 2 | A1943 | 350.39 | APCI (m/z) 351.15 (M$^+$) | $^1$H NMR (500 MHz, DMSO-d6) δ 9.26 (dd, J = 4.1, 1.5 Hz, 1H), 8.63 (d, J = 8.3 Hz, 1H), 8.45 (d, J = 8.2 Hz, 1H), 8.35 (d, J = 7.3 Hz, 1H), 7.88 (s, 1H), 7.82 (dd, J = 8.3, 4.2 Hz, 1H), 7.73 (t, J = 7.8 Hz, |

TABLE 2-continued

| Examples | Compound Number | MW | LCMS | NMR |
|---|---|---|---|---|
| | | | | 1H), 7.57 (d, J = 9.0 Hz, 1H), 7.18 (t, J = 7.7 Hz, 1H), 7.00 (d, J = 8.2 Hz, 1H), 6.80-6.76 (m, 1H), 6.67 (d, J = 7.5 Hz, 1H), 5.73 (s, 2H). |
| 3 | A1944 | 344.35 | APCI (m/z) 345.10 (M$^+$) | $^1$H NMR (500 MHz, DMSO-d6) δ 9.85 (s, 1H), 9.15 (dd, J = 4.2, 1.8 Hz, 1H), 8.53 (dd, J = 8.4, 1.7 Hz, 1H), 8.28-8.23 (m, 2H), 8.00 (d, J = 2.8 Hz, 1H), 7.76-7.70 (m, 1H), 7.67 (dd, J = 8.0, 7.6 Hz, 1H), 7.40 (d, J = 2.7 Hz, 1H), 7.10 (dd, J = 8.9, 2.8 Hz, 1H), 7.08 (d, J = 9.0 Hz, 1H), 6.69 (d, J = 8.9 Hz, 1H). |
| 4 | A1948 | 349.41 | ESI (m/z) 350.00 (M$^+$) | 1H NMR (500 MHz, DMSO-d6) δ 10.00 (s, 1H), 7.76 (d, J = 2.7 Hz, 1H), 7.60 (d, J = 8.5 Hz, 2H), 7.55 (d, J = 8.5 Hz, 2H), 7.49-7.43 (m, 1H), 7.23 (dd, J = 8.8, 2.6 Hz, 1H), 7.06 (d, J = 8.8 Hz, 1H), 6.85 (d, J = 8.9 Hz, 1H), 1.26 (s, 9H). |
| 5 | A1949 | 375.45 | ESI (m/z) 376.00 (M$^+$), 417.05 (MAc$^+$) | $^1$H NMR (500 MHz, DMSO-d6) δ 8.05 (d, J = 8.6 Hz, 1H), 7.99 (d, J = 8.7 Hz, 2H), 7.94 (d, J = 8.7 Hz, 2H), 7.77-7.70 (m, 2H), 7.52 (dd, J = 10.5, 4.2 Hz, 2H), 7.49-7.44 (m, 1H), 7.36-7.30 (m, 1H), 7.19 (t, J = 8.0 Hz, 2H), 7.02 (d, J = 8.3 Hz, 1H), 6.68 (d, J = 6.9 Hz, 1H), 5.91 (s, 2H). |
| 6 | A1950 | 313.38 | ESI (m/z) 314.00(M$^+$), 455.0 (MAc$^+$) | $^1$H NMR (500 MHz, DMSO-d6) δ 8.08 (d, J = 8.1 Hz, 1H), 7.81 (dd, J = 8.4, 2.0 Hz, 3H), 7.61-7.52 (m, 2H), 7.45 (d, J = 8.1 Hz, 2H), 7.14 (d, J = 6.5 Hz, 1H), 7.10 (d, J = 8.1 Hz, 1H), 2.41 (s, 3H). |
| 7 | A1880 | 299.35 | ESI (m/z) 341.00 (MAc$^+$) 382.05 (M2Ac$^+$) | $^1$H NMR (500 MHz, DMSO-d6) δ 8.50 (d, 1H, J = 2.0 Hz), 8.21-8.18 (m, 2H), 8.10 (d, 1H, J = 8.0 Hz), 7.82 (dd, 1H, J = 2.0, 8.5 Hz), 7.78 (td, 1H, J = 1.5, 7.0 Hz), 7.70 (td, 1H, J = 1.5, 7.0 Hz), 6.61 (d, 2H, J = 9.0 Hz), 6.38 (d, 2H, J = 9.0 Hz), 5.19 (s, 2H) |
| 8 | A1881 | 313.38 | ESI (m/z) 313.95 (M$^+$) 355.00 (MAc$^+$) | $^1$H NMR (500 MHz, DMSO-d6) δ 8.02 (d, 1H, J = 8.5 Hz), 7.80 (d, 1H, J = 8.0 Hz), 7.44 (d, 2H, J = 8.0 Hz), 7.30 (t, 1H, J = 8.5 Hz), 7.19 (t, 1H, J = 8.5 Hz), 7.11 (d, 1H, J = 7.5 Hz), 7.00 (d, 1H, J = 8.0 Hz), 6.68 (d, 1H, J = 7.5 Hz), 5.89 (s, 2H), 2.39 (s, 3H) |
| 9 | A1882 | 313.38 | ESI (m/z) 314.00 (M$^+$) 355.00 (MAc$^+$) | $^1$H NMR (500 MHz, DMSO-d6) δ 7.86 (d, 1H, J = 2.5 Hz), 7.75 (d, 2H, J = 8.5 Hz), 7.69 (d, 2H, J = 9.0 Hz), 7.46 (d, 2H, J = 8.0 Hz), 7.22 (t, 1H, J = 7.7 Hz), 7.06 (d, 1H, J = 8.0 Hz), 6.93 (dd, 1H, J = 2.5, 9.0 Hz), 6.69 (d, 1H, J = 7.5 Hz), 5.76 (s, 2H), 2.41 |
| 10 | A1999 | 305.40 | ESI (m/z) 306.05 (M$^+$) | $^1$H NMR (500 MHz, DMSO-d6) δ 10.16 (s, 1H), 9.43 (s, 1H), 7.70 (d, 1H, J = 8.3 Hz), 7.57 (d, 2H, J = 8.0 Hz), 6.97 (t, 1H, J = 8.0 Hz), 6.60 (s, 1H), 6.53 (d, 1H, J = 8.0 Hz), 6.38 (d, 1H, J = 8.0 Hz), 1.26 (s, 9H) |
| 11 | A2000 | 339.84 | ESI (m/z) 340.05 (M$^+$ − 1), 342.05 (M$^+$ + 1), 381.05 (MAc$^-$ − 1), 383.05 (MAc$^+$ + 1) | $^1$H NMR (500 MHz, DMSO-d6) δ 7.71 (q, 4H, J = 9.0 Hz), 6.77 (t, 1H, J = 1.2 Hz), 6.68 (d, 2H, J = 1.5 Hz), 5.51 (s, 2H), 1.30 (s, 9H) |
| 12 | A2001 | 359.83 | ESI (m/z) 360.00 (M$^+$), 401.00 (MAc$^+$) | $^1$H NMR (500 MHz, DMSO-d6) δ 7.97 (d, 2H, J = 8.5 Hz), 7.89 (d, 2H, J = 8.5 Hz), 7.78 (d, 2H, J = 7.5 Hz), 7.53 (t, 2H, J = 7.5 Hz), 7.47 (q, 1H, J = 7.0 Hz), 6.56 (d, 1H, J = 2.0 Hz), 6.72-6.68 (m, 2H), |
| 13 | A2002 | 333.80 | ESI (m/z) 334.05 (M$^+$ − 1), 336.05 (M$^+$ + 1), 374.95 (MAc$^+$ − 1), 376.95 (MAc$^+$ + 1) | $^1$H NMR (500 MHz, DMSO-d6) δ 8.54 (s, 1H), 8.23-8.21 (m, 2H), 8.12 (d, 1H, J = 8.0 Hz), 7.83 (dd, 1H, J = 2.0, 8.5 Hz), 7.79 (t, 1H, J = 7.5 Hz), 7.71 (tm, 1H, J = 7.5 Hz), 6.91 (s, 1H), 6.62 (s, 2H), 5.49 (s, 2H) |
| 14 | A2007 | 323.39 | ESI (m/z) 324.00 (M$^+$), 365.05 (MAc$^+$) | $^1$H NMR (500 MHz, DMSO-d6) δ 7.74 (d, 2H, J = 9.0 Hz), 7.67 (d, 2H, J = 8.5 Hz), 6.69 (dd, 1H, J = 2.5, 11.5 Hz), 6.94 (t, 1H, J = 9.5 Hz), 6.53 (dd, 1H, J = 2.5, 9.0 Hz), 5.29 (s, 2H), 1.26 (s, 9H) |
| 15 | A2008 | 343.38 | ESI (m/z) 344.00 (M$^+$), 385.05 (MAc$^+$) | $^1$H NMR (500 MHz, DMSO-d6) δ 7.96 (d, 2H, J = 8.5 Hz), 7.87 (d, 2H, J = 8.5 Hz), 7.78 (d, 2H, J = 7.0 Hz), 7.53 (t, 2H, J = 7.1 Hz), 7.47 (t, 1H, J = 7.2 Hz), 6.78 (dd, 1H, J = 2.5, 11.5.0 Hz), 6.64 (t, 1H, J = 8.5 Hz), 6.57 (d, 1H, J = 9.0 Hz), 5.31 (s, 2H) |
| 16 | A2009 | 317.34 | ESI (m/z) 318.00 (M$^+$), 359.05 (MAc$^+$) | $^1$H NMR (500 MHz, DMSO-d6) δ 8.53 (s, 1H), 8.22-8.20 (m, 2H), 8.11 (d, 1H, J = 8.5 Hz), 7.83 (d, 2H, J = 7.5 Hz), 7.79 (t, 1H, J = 7.5 Hz), 7.71 (t, 1H, J = 7.5 Hz), 6.76 (dd, 1H, J = 2.3, 11.8 Hz), 6.59 (t, 1H, J = 9.5 Hz), 6.50 (d, 1H, J = 9.0 Hz), 5.27 (s, |

TABLE 2-continued

| Exmaples | Compound Number | MW | LCMS | NMR |
|---|---|---|---|---|
| 17 | A2010 | 323.39 | ESI (m/z) 324.00 (M⁺), 346.00 (MNa⁺) | ¹H MMR (500 MHz, DMSO-d6) δ 7.75 (d, 2H, J = 8.5 Hz), 7.69 (d, 2H, J = 8.5 Hz), 6.71 (t, 1H, J = 9.5 Hz), 6.52 (dd, 1H, J = 2.5, 13.0 Hz), 6.26 (dd, 1H, J = 2.5, 9.0 Hz), 5.54 (s, 2H), 1.31 (s, 9H) |
| 18 | A2011 | 343.38 | ESI (m/z) 344.00 (M⁺), 366.00 (MNa⁺) | ¹H NMR (500 MHz, DMSO-d6) δ 7.98 (d, 2H, J = 8.5 Hz), 7.89 (d, 2H, J = 8.5 Hz), 7.79 (d, 2H, J = 7.0 Hz), 7.54 (t, 2H, J = 7.5 Hz), 7.47 (q, 3H, J = 7.5 Hz), 6.82 (t, 1H, J = 8.8 Hz), 6.43 (d, 1H, J = 13.0 Hz), 6.36 (d, 1H, J = 8.5 Hz) |
| 19 | A2012 | 317.34 | ESI (m/z) 318.00 (M⁺), 359.05 (MAc⁺) | ¹H NMR (500 MHz, DMSO-d6) δ 8.56 (s, 1H), 8.22 (t, 2H, J = 8.5 Hz), 8.12 (d, 1H, J = 9.5 Hz), 7.85-7.78 (m, 3H), 7.73-7.70 (m, 2H), 6.75 (d, 1H, J = 8.5 Hz), 6.37 (d, 1H, J = 13.0 Hz), 6.31 (d, 1H, J = 9.0 Hz) |
| 20 | A2013 | 344.35 | ESI (m/z) 345.00 (M⁺), 367.05 (MNa⁺) | ¹H NMR (500 MHz, DMSO-d6) δ 8.51 (s, 1H), 8.23-8.21 (m, 2H), 8.12 (d. 1H, J = 8.0 Hz), 7.82-7.76 (m, 2H), 7.72 (t, 1H, J = 7.5 Hz), 7.05 (d, 1H, J = 2.5 Hz), 6.73 (d, 1H, J = 9.0 Hz), 6.68 (dd, 1H, J = 2.5, 9.0 Hz), 5.92 (s, 1H), 3.36 (s, 1H) |
| 21 | A2062 | 349.45 | ESI (m/z) 350.10 (M⁺), 372.15 (MNa⁺) | ¹H NMR (500 MHz, DMSO-d6) δ 7.61 (d, 2H, J = 8.0 Hz), 7.51 (d, 2H, J = 8.0 Hz), 6.50 (d, 1H, J = 8.0 Hz), 6.42 (s, 1H), 6.27 (d, 1H, J = 8.0 Hz), 4.17 (t, 1H, J = 7.0 Hz), 2.74 (t, 2H, J = 7.8 Hz), 2.39 (d, 1H, J = 7.5 Hz), 2.08-2.02 (m, 1H), 1.21 (s, 9H) |
| 22 | A2063 | 369.44 | ESI (m/z) 370.10 (M⁺), 392.15 (MNa⁺) | ¹H NMR (500 MHz, DMSO-d6) δ 8.62 (d, 2H, J = 33.5 Hz), 7.77 (q, 4H, J = 8.5 Hz), 7.66-7.62 (m, 3H), 7.42 (t, 2H, J = 7.5 Hz), 7.35 (t, 1H, J = 7.5 Hz), 6.51 (d, 1H, J = 8.0 Hz), 6.43 (d, 1H, J = 2.0 Hz), 6.29 (dd, 1H, J = 2.0, 8.0 Hz), 2.80 (q, 2H, J = 6.5 Hz), 2.44-2.41 (m, 2H) |
| 23 | A2064 | 343.40 | ESI (m/z) 344.05 (M⁺), 366.10 (MNa⁺) | ¹H NMR (500 MHz, DMSO-d6) δ 8.69 (br s, 1H), 8.42 (s, 1H), 8.16 (d, 1H, J = 8.0 Hz), 8.12 (d, 1H, J = 9.0 Hz), 8.04 (d, 2H, J = 8.5 Hz), 7.81 (d, 1H, J = 8.5 Hz), 7.75-7.65 (m, 3H), 6.57 (d, 1H, J = 8.0 Hz), 6.50 (s, 1H), 6.34 (d, 1H, J = 8.0 Hz), 2.89 (t, 2H, J = 7.5 Hz), 2.47 (d, 2H, J = 7.5 Hz) |
| 24 | A2065 | 347.48 | ESI (m/z) 348.10 (M⁺), 389.15 (MAc⁺) | ¹H NMR (500 MHz, DMSO-d6) δ 7.68 (d, 2H, J = 9.0 Hz), 7.59 (d, 2H, J = 8.5 Hz), 6.83 (d, 1H, J = 8.0 Hz), 6.12 (dd, 1H, J = 2.5, 8.0 Hz), 5.69 (d, 1H, J = 2.0 Hz), 4.05 (s, 1H), 2.72-2.67 (m, 2H), 1.90 (s, 3H), 1.21 (s, 9H), 0.88 (t, 3H, J = 6.0 Hz) |
| 25 | A2066 | 341.43 | ESI (m/z) 342.05 (M⁺), 383.10 (MAc⁺) | ¹H NMR (500 MHz, DMSO-d6) δ 8.56 (s, 1H), 8.21 (d, 2H, J = 9.0 Hz), 8.10 (d, 1H, J = 8.5 Hz), 7.89 (d, 1H, J = 8.5 Hz), 7.78 (t, 1H, J = 7.5 Hz), 7.70 (t, 1H, J = 7.5 Hz), 6.85 (d, 1H, J = 8.0 Hz), 6.13 (dd, 1H, J = 2.5, 8.0 Hz), 6.95 (d, 1H, J = 2.0 Hz), 5.01 (t, 1H, J = 5.5 Hz), 2.78-2.72 (m, 2H), 1.95 (s, 3H), 0.85 (t, 3H, J = 7.0 Hz) |
| 26 | A2067 | 339.50 | ESI (m/z) 340.20 (M⁺), 362.20 (MNa⁺) | ¹H NMR (500 MHz, DMSO-d6) δ 7.72 (t, 2H, J = 8.3 Hz), 7.58 (dd, 2H, J = 2.0, 8.5 Hz), 7.55-7.50 (m, 1H), 4.29-4.27 (m, 1H), 3.39-3.36 (m, 1H), 2.50 (s, 2H), 1.60 (t, 2H, J = 11.0 Hz), 1.42 (s, 1H), 1.33-1.20 (m, 15H), 1.11 (d. 1H, J = 9.5 Hz), 0.79 (q, 1H, J = 10.5 Hz) |
| 27 | A2068 | 359.49 | ESI (m/z) 360.20 (M⁺) | ¹H NMR (500 MHz, DMSO-d6) δ 7.88 (d, 4H, J = 4.5 Hz), 7.75 (d, 2H, J = 7.5 Hz), 7.68-7.64 (m, 1H), 7.51 (t, 2H, J = 7.5 Hz), 7.44 (t, 1H, J = 7.2 Hz), 4.30-4.25 (m, 1H), 3.40-3.34 (m, 2H), 2.91-2.85 (m, 1H), 1.62 (t, 2H, J = 15.3 Hz), 1.49-1.43 (m, 2H), 1.35-1.32 (m, 3H), 1.21 (s, 2H), 1.13 (d, 1H, J = 12.0 Hz), 0.81 (q, 1H, J = 11.0 Hz) |
| 28 | A2069 | 333.45 | ESI (m/z) 334.15 (M⁺), 356.10 (MNa⁺) | ¹H NMR (500 MHz, DMSO-d6) δ 8.43 (s, 1H), 8.15 (d, 1H, J = 8.0 Hz), 8.12 (d, 1H, J = 9.0 Hz), 8.03 (d, 1H, J = 8.0 Hz), 7.88-7.82 (m, 1H), 7.71-7.65 (m, 3H), 4.27-4.23 (m, 1H), 3.18 (s, 1H), 3.38-3.30 (m, 2H), 1.57 (t, 2H, J = 13.2 Hz), 1.40-1.30 (m, 6H), 1.21-1.18 (m, 1H), 1.20 (d, 1H, J = 12.0 Hz), 0.81 (q, 1H, J = 11.0 Hz) |

Experimental Example 1

Confirmation of Differentiation of Mesenchymal Stem Cells to Chondrocytes by Compound of Formula 1

Separation and Incubation of Human Fat-Derived Mesenchymal Stem Cells 60 cc of an expanding solution (obtained by adding 30 mL of 1% lidocaine, 30 mL of 0.5% bupivacaine, 10 mL of 4.2% sodium bicarbonate and 1 mg of epinephrine to 1 L of normal water for injection) was applied to the periphery of a navel under sterile conditions. Fats were suctioned using Mercedes 3 mm×9 cm Aspiration Luer Lock Cannula (Byron Medical, Tucson, Ariz.), and then instantly kept on ice. Since a lipoaspirate filtered through a 250 mm sieve included an anesthetic and a contaminant such as blood, the lipoaspirate was washed with phosphate buffered saline (PBS) to remove the anesthetic and the contaminant. Collagenase I (1 mg/mL; Worthington Biochemical Corp., Lakewood, N.J.) was added to the obtained fat tissues, stirred, and then kept at 37° C. for an hour. The suspended adipose tissues were centrifuged at 1,500×g for 10 minutes, and a supernatant containing matured fat cells was discarded. The obtained stroma vascular (SV) cells were washed with 0.1% BSA, suspended in an M-199 medium (including 12.8% fetal bovine serum, heparin, 10,000 U/mL penicillin G, 25 mg/mL amphotericin B, and 10,000 mg/mL streptomycin), plated on a gelatin-coated tissue culture flask, and then incubated. After 24 hours, the tissue culture flask was washed to remove non-attached cells, and the incubation was continued.

Ex Vivo Modification of Mesenchymal Stem Cells by Treatment with Compound

When the mesenchymal stem cells were subcultured twice, the mesenchymal stem cells were seeded at a density of $2\times10^5$ cells/ml in a 60 mm plate containing the same medium as described above, and treated with the compound of Formula 1 (each of the compounds of Examples 1 to 28) at a final concentration of 10 nM, 100 nM, 1 μM, or 10 μM. In this case, the mesenchymal stem cells were incubated for 11 days while replacing a medium including the compound of Formula 1 with a fresh one once every 3 days.

Alcian Blue Dyeing

Cells were first washed three times with PBS (Gibco), and then immobilized with 100% methanol (Sigma) at −20° C. for 10 minutes. Dyeing was performed by treating the cells with a 0.1 M HCl (pH 1.0) solution comprising 1% Alcian Blue 8GX (Bio Basis, Ontario, Canada) at room temperature for 2 hours. To quantify the dyeing intensity, the dyed culture plate was washed three times with PBS, and each well was extracted with 1 ml of 6 M guanidine-HCl (Sigma) overnight at room temperature. The optical density of the extracted dye was measured at 650 nm.

Sandwich ELISA

A capture antibody was bound to the bottom of each well, and the plate was then incubated overnight at 4° C. The plate was washed twice with PBS (Gibco), and treated with 100 μl of PBS containing 3% BSA at room temperature for 2 to 3 hours. The plate was washed twice with PBS, and a cell lysate was added to each well. Then, the plate was incubated at room temperature for 2 hours under a wet atmosphere. The plate was washed four times with PBS containing 0.02% Tween-20 (Sigma). A detector antibody was added to the plate, and the plate was then incubated at room temperature for 2 hours under a wet atmosphere. Thereafter, the plate was incubated with a peroxidase-conjugated secondary antibody at 37° C. for an hour. Finally, the plate was treated with 100 μl of a tetramethylbenzidine (TMB) solution (Sigma) as a substrate, and 25 μl of 0.1 M $H_2SO_4$ was added as a terminating buffer to stop the reaction. Immediately after the reaction, the absorbance was measured at 450 nm using an ELISA plate reader (Bio-Rad).

Western Blotting

Cells were washed once with PBS, and lysed for approximately 20 minutes in a lysis buffer (Cell Signaling Technology) containing 20 mM Tris (pH 7.5), 150 mM NaCl, 1 mM $Na_2$-EDTA, 1 mM EGTA, 1% Triton, 2.5 mM sodium pyrophosphate, 1 mM β-glycerophosphate, 1 mM $Na_3VO_4$, 1 mg/ml leupeptin and 1 mM phenylmethylsulfonyl fluoride. The cell lysate was centrifuged at 12,000 g for 10 minutes to obtain a supernatant. A concentration of proteins was measured using a Bradford protein assay kit (Bio-Rad). A quantitative protein was separated on a 12% sodium dodecyl sulfate-polyacrylamide gel, and transferred to a polyvinylidene difluoride membrane (Millipore). The membrane was blocked with Tris-buffered saline-Tween 20 (TBS-T, 0.1% Tween 20) containing 5% fat-free powdered milk, and then washed twice with TBS-T. Then, the membrane was incubated overnight at 4° C. with a primary antibody (ERK and p-ERK; Santa Cruz Biotechnology). The membrane was washed three times with TBS-T for 10 minutes, and then incubated at room temperature for an hour with a horseradish peroxidase-conjugated secondary antibody. After thorough washing, a band was detected using an improved chemiluminogenic reagent (GE Healthcare Life Sciences). The intensity of the band was quantified using an Image J 1.40 g software (NIH).

RT-PCR

Expression levels of various genes were analyzed through an RT-PCR method. Total RNA was obtained using an Ultraspect™-II RNA system (Biotecx Laboratories, Inc., USA) and an easy-BLUE™ kit (Intron Biotechnology, Seoul, South Korea). Single-stranded cDNA was synthesized from the separated total RNA using Avian Myeloblastosis virus (AMV) reverse transcriptase (Powver cDNA Synthesis Kit, Intron Biotechnology). 20 μl of a reverse transcriptase reaction mixture containing 1 μl of the total RNA, 1× reverse transcriptase buffer (10 mM Tris-HCl, pH 9.0, 50 mM KCl, 0.1% Triton X-100), 1 mM deoxynucleoside triphosphate (dNTPs), 0.5 units of an RNase inhibitor, 0.5 μg of oligo(dT) 15, and 15 units of AMV reverse transcriptase was incubated at 42° C. for 15 minutes, and heated at 99° C. for 5 minutes. Then, the resulting mixture solution was incubated at 0 to 5° C. for 5 minutes. PCR using Tap polymerase (i-Max™ DNA polymerase, Intron Biotechnology) was performed according the standard method. The PCR was performed for 25 to 45 cycles, as follows: denaturation at 94° C. for 30 seconds, annealing at 58 to 65° C. for 30 seconds, and extension at 72° C. for 30 seconds. Primers used herein are as follows.

```
Fibronectin:
5'-CCTTAAGCCTTCTGCTCTGG-3',           (SEQ ID NO: 1)
and

5'-CGGCAAAAGAAAGCAGAACT-3'            (SEQ ID NO: 2)
(300 bp);

β1-integrin:
5'-GCCAGTGTCACCTGGAAAAT-3',           (SEQ ID NO: 3)
and

5'-TCGTCCATTTTCTCCTGTCC-3'            (SEQ ID NO: 4)
(344 bp);
```

-continued

```
α5-integrin:
5'-CTTCGGTTCACTGTTCCTC-3',            (SEQ ID NO: 5)
and

5'-TGGCTTCAGGGCATTT-3' (283 bp);      (SEQ ID NO: 6)
and

N-cadherin:
5'-GCCACCATATGACTCCCTTTTAGT-3',       (SEQ ID NO: 7)
and

5'-CAGAAAACTAATTCcAATCTGAAA-3'        (SEQ ID NO: 8)
(454 bp).

GAPDH primers
(5'-CTCCCAACGTGTCTGTTGTG-3',          (SEQ ID NO: 9)

5'-TGAGCTTGACAAAGTGGTCG-3' (450 bp)   (SEQ ID NO: 10)
and

5'-ACCACAGTCcATGCCATCA-3',            (SEQ ID NO: 11)

5'-TCCACCACCCTGTTGCTGTA-3'            (SEQ ID NO: 12)
(450 bp))
```

Glyceraldehyde 3-phosphate dehydrogenase (GAPDH) were used for internal standardization. The signal intensities of amplified products were normalized as relative intensities of the amplified products with respect to the signal intensity of GAPDH.

Statistical Analysis

The results were indicated by the standard error of the mean (SEM), and compared using a Student's t-test. The correlation was considered to be statistically significant when a p-value was less than 0.05.

Results

To test whether the compound of Formula 1 may induce differentiation of mesenchymal stem cells to chondrocytes, the present inventors quantified chondrogenesis through Alcian Blue dyeing of sulfated proteoglycan. As a result, it was revealed that the treated group in which the mesenchymal stem cells were treated with the A1942 compound (1 µM) for 11 days showed relative absorbance approximately 3 times higher than the control ((*$p<0.05$ vs. control), as shown in FIG. 1.

Figure 2:
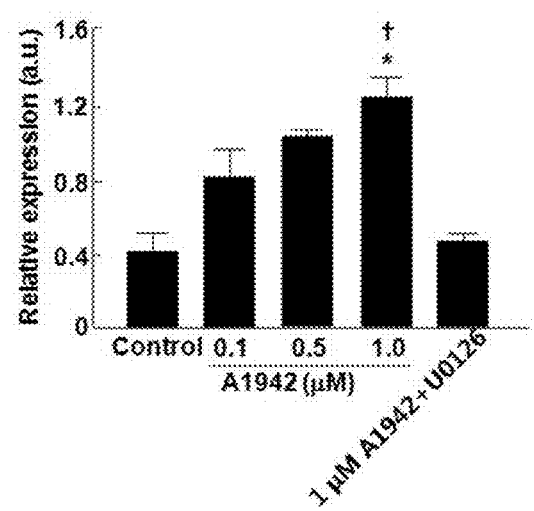
FIG. 2 shows the sandwich enzyme-linked immunosorbent assay (ELISA) results indicating that the compound of Formula 1 induces differentiation of mesenchymal stem cells to chondrocytes in a dose-dependent manner.

To determine whether the mesenchymal stem cells treated with various concentrations of the A1942 compound were differentiated to chondrocytes in a dose-dependent manner, the present inventors also conducted research on up-regulated expression of aggrecan which was a chondrocyte marker. The mesenchymal stem cells were treated with various concentrations of the A1942 compound (0.1, 0.5, and 1 µM) for 11 days. As a result, it was assumed that induction of chondrogenesis by the compound of Formula 1 was mediated with (ERK) MAP kinase signaling pathway. Therefore, an effect of U0126, which was a selective inhibitor of MEK, on expression of aggrecan was also examined. A change in expression level of the aggrecan during chondrogenesis of the mesenchymal stem cells was also examined using sandwich ELISA. As a result, it was assumed that an expression level of the aggrecan was increased in a dose-dependent manner according to an increasing concentration of the treated A1942 compound, and treatment of the mesenchymal stem cells with U0126, which was a selective inhibitor of MEK, reduced an expression level of the aggrecan even when the mesenchymal stem cells were treated with the A1942 compound (*$p<0.05$ vs. control, †$p<0.01$ vs. 1 µM A1942+U0126), as shown in FIG. 2.

Figure 3:
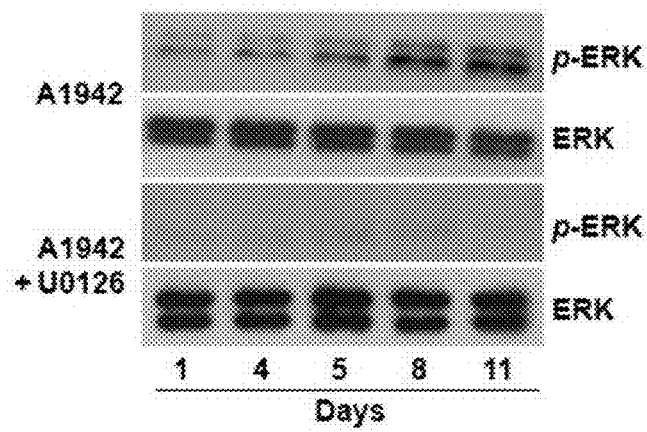
FIG. 3 shows the western blot results indicating that the compound of Formula 1 phosphorylates extracellular regulated kinase (ERK).

Also, the present inventors conducted research on an effect of the A1942 compound on phosphorylation of ERK. During chondrogenesis of the mesenchymal stem cells treated with 1 µM of the A1942 compound for 11 days, a change in phosphorylation level of ERK was examined using western blotting. As a result, it was revealed that the phosphorylation level of ERK increased with time in the case of the A1942-treated group, but did not increase with time in the case of the group treated with the A1942 and U0126 compounds, as shown in FIG. 3.

Figure 4:
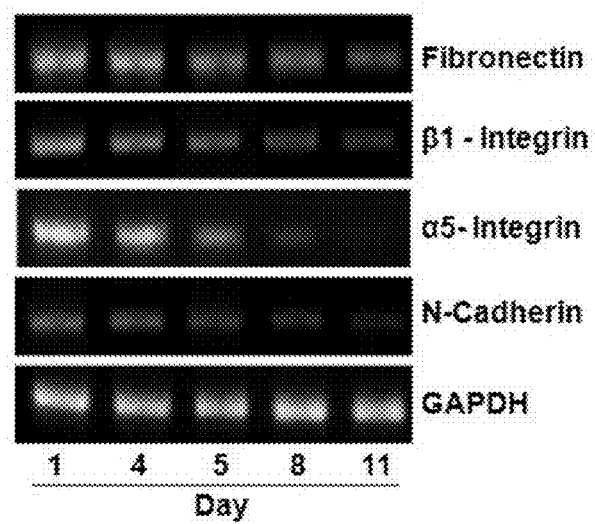
FIG. 4 shows the semi-quantitative reverse transcription polymerase chain reaction (RT-PCR) results indicating an effect of the compound of Formula 1 on fibronectin, integrin α5β1 and N-cadherin in which an interaction between cells and an extracellular substrate (ECM) and a cell-cell interaction are associated with regulation of differentiation to chondrocytes.

The interaction between cells and an extracellular substrate (ECM) and the cell-cell interaction were associated with regulation of differentiation to chondrocytes. Therefore, an effect of the compound of Formula 1 on expression levels of integrin α5β1 mediating interaction between cells and an ECM, fibronectin which is a ligand for the integrin α5β1, and N-cadherin mediating cell-cell interaction during chondrogenesis of the mesenchymal stem cells, which were treated with 1 µM of the A1942 compound for 11 days, was examined using semi-quantitative RT-PCR. As a result, it was confirmed that the expression levels of fibronectin, α5-integrin and N-cadherin decreased with time, as shown in FIG. 4.

Figure 5:
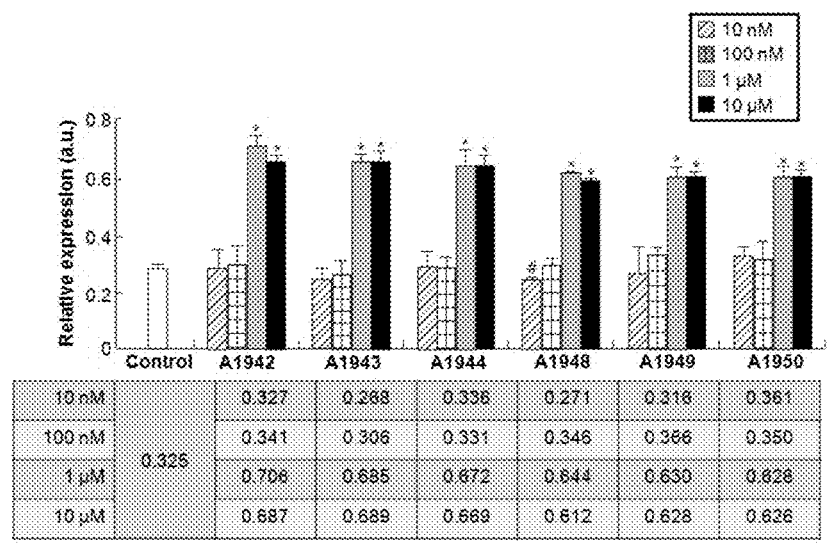
FIG. 5 shows the sandwich ELISA results indicating that A1943, A1944, A1948, A1949 and A1950 compounds induce differentiation of mesenchymal stem cells to chondrocytes at a level similar to an A1942 compound.

In addition, the present inventors conducted research on effects of other compounds of Formula 1 rather than the A1942 compound on induction of differentiation to chondrocytes. A change in expression level of the aggrecan during chondrogenesis of the mesenchymal stem cells was examined in the same manner as described above using sandwich ELISA. As a result, it was assumed that the A1943, A1944, A1948, A1949 and A1950 compounds (compounds of Examples 2 to 6) induced differentiation of mesenchymal stem cells to chondrocytes at a level similar to the A1942 compound (One-way analysis of variance, Bonferroni's Multiple Comparison Test (*$p<0.001$ vs. control)), as shown in FIG. 5.

Furthermore, the present inventors conducted research on effects of the synthesized compounds of Examples 7 to 28 on induction of differentiation to chondrocytes in the same manner as in the sandwich ELISA. As a result, it was assumed that the compounds of Example 7 to 28 also induced differentiation of mesenchymal stem cells to chondrocytes at a level similar to the A1942 compound, as listed in the following Table 3. In Table 3, the chondrocyte differentiation-inducing activities were normalized with respect to the control.

TABLE 3

| Examples | Compound Number | Chondrocyte differentiation-inducing activities | |
|---|---|---|---|
| | | 1 µM | 10 µM |
| 1 | A1942 | 0.350 | 0.330 |
| 2 | A1943 | 0.328 | 0.333 |
| 3 | A1944 | 0.316 | 0.313 |
| 4 | A1948 | 0.287 | 0.256 |
| 5 | A1949 | 0.273 | 0.272 |
| 6 | A1950 | 0.271 | 0.270 |
| 7 | A1880 | 0.044 | 0.069 |
| 8 | A1881 | 0.094 | 0.075 |
| 9 | A1882 | 0.062 | 0.060 |
| 10 | A1999 | | 0.357 |
| 11 | A2000 | | 0.397 |
| 12 | A2001 | | 0.444 |
| 13 | A2002 | | 0.443 |
| 14 | A2007 | 0.001 | 0.332 |
| 15 | A2008 | | 0.382 |
| 16 | A2009 | | 0.420 |
| 17 | A2010 | | 0.427 |
| 18 | A2011 | | 0.294 |
| 19 | A2012 | | 0.364 |
| 20 | A2013 | | 0.415 |
| 21 | A2062 | 0.029 | 0.064 |

TABLE 3-continued

| Examples | Compound Number | Chondrocyte differentiation-inducing activities | |
|---|---|---|---|
| | | 1 μM | 10 μM |
| 22 | A2063 | 0.030 | 0.074 |
| 23 | A2064 | | 0.071 |
| 24 | A2065 | | 0.081 |
| 25 | A2066 | 0.013 | 0.077 |
| 26 | A2067 | | 0.070 |
| 27 | A2068 | | 0.076 |
| 28 | A2069 | 0.001 | 0.059 |

The invention claimed is:

1. A method of inducing differentiation of mesenchymal stem cells to chondrocytes, comprising: incubating the mesenchymal stem cells in a medium comprising at least one compound selected from the group consisting of:
   1) quinoline-8-sulfonic acid (4-hydroxy-phenyl)-amide;
   2) quinoline-8-sulfonic acid (7-hydroxy-naphthalen-1-yl)-amide;
   3) 2-hydroxy-5-(quinoline-8-sulfonylamino)-benzoic acid;
   4) 5-(4-tert-butyl-benzenesulfonylamino)-2-hydroxy-benzoic acid;
   5) biphenyl-4-sulfonic acid (5-hydroxy-naphthalen-1-yl)-amide;
   6) N-(4-hydroxy-naphthalen-1-yl)-4-methyl-benzenesulfonamide;
   7) naphthalene-2-sulfonic acid (4-hydroxyl-phenyl)-amide;
   8) N-(5-hydroxyl-naphthalen-1-yl)-4-methyl-benzenesulfonamide;
   9) N-(7-hydroxyl-naphthalen-1-yl)-4-methyl-benzenesulfonamide;
   10) 4-tert-butyl-N-(3-hydroxyl-phenyl)-benzenesulfonamide;
   11) 4-tert-butyl-N-(2-chloro-4-hydroxyl-phenyl)-benzenesulfonamide;
   12) biphenyl-4-sulfonic acid (2-chloro-4-hydroxyl-phenyl)-amide;
   13) naphthalene-2-sulfonic acid (2-chloro-4-hydroxyl-phenyl)-amide;
   14) 4-tert-butyl-N-(2-fluoro-4-hydroxyl-phenyl)-benzenesulfonamide;
   15) biphenyl-4-sulfonic acid (2-fluoro-4-hydroxyl-phenyl)-amide;
   16) naphthalene-2-sulfonic acid (2-fluoro-4-hydroxyl-phenyl)-amide;
   17) 4-tert-butyl-N-(3-fluoro-4-hydroxyl-phenyl)-benzenesulfonamide;
   18) biphenyl-4-sulfonic acid (3-fluoro-4-hydroxyl-phenyl)-amide;
   19) naphthalene-2-sulfonic acid (3-fluoro-4-hydroxyl-phenyl)-amide;
   20) naphthalene-2-sulfonic acid (3-nitro-4-hydroxyl-phenyl)-amide;
   21) 4-tert-butyl-N-[2-(3,4-dihydroxyl-phenyl)-ethyl]-benzenesulfonamide;
   22) biphenyl-4-sulfonic acid [2-(3,4-dihydroxyl-phenyl)-ethyl]-amide;
   23) naphthalene-2-sulfonic acid [2-(3,4-dihydroxyl-phenyl)-ethyl]-amide;
   24) 4-tert-butyl-N-ethyl-N-(5-hydroxyl-2-methyl-phenyl)-benzenesulfonamide;
   25) naphthalene-2-sulfonic acid ethyl-(5-hydroxyl-2-methyl-phenyl)-amide;
   26) 4-tert-butyl-N-[4-(2-hydroxyl-ethyl)-cyclohexyl]-benzenesulfonamide;
   27) biphenyl-4-sulfonic acid [4-(2-hydroxyl-ethyl)-cyclohexyl]-amide; and
   28) naphthalene-2-sulfonic acid [4-(2-hydroxyl-ethyl)-cyclohexyl]-amide.

2. The method of claim 1, wherein the mesenchymal stem cells are derived from bone marrow, tissue, an embryo, cord blood, blood, or body fluid.

3. The method of claim 1, wherein the mesenchymal stem cells are incubated for 5 to 15 days.

4. The method of claim 1, wherein an expression level of fibronectin, β1-integrin, α5-integrin or N-cadherin is decreased in the chondrocytes, compared to the mesenchymal stem cells.

* * * * *

SEQUENCE LISTING

<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
ccttaagcct tctgctctgg                                          20

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
cggcaaaaga aagcagaact                                          20

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
gccagtgtca cctggaaaat                                          20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
tcgtccattt tctcctgtcc                                          20

<210> SEQ ID NO 5
<211> LENGTH: 19
<212> TYPE: DNA
<213> ORGANISM: Artificial Sequence
<220> FEATURE:
<223> OTHER INFORMATION: Primer

<400> SEQUENCE: 5
cttcggttca ctgttcctc                                           19

<210> SEQ ID NO 6
<211> LENGTH: 16

```
<212> TYPE: DNA
<213> ORGANISM: Artificial Sequence
<220> FEATURE:
<223> OTHER INFORMATION: Primer

<400> SEQUENCE: 6
tggcttcagg gcattt                                                          16

<210> SEQ ID NO 7
<211> LENGTH: 24
<212> TYPE: DNA
<213> ORGANISM: Artificial Sequence
<220> FEATURE:
<223> OTHER INFORMATION: Primer

<400> SEQUENCE: 7
gccaccatat gactcccttt tagt                                                 24

<210> SEQ ID NO 8
<211> LENGTH: 24
<212> TYPE: DNA
<213> ORGANISM: Artificial Sequence
<220> FEATURE:
<223> OTHER INFORMATION: Primer

<400> SEQUENCE: 8
cagaaaacta attccaatct gaaa                                                 24

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
ctcccaacgt gtctgttgtg                                                      20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
tgagcttgac aaagtggtcg                                                      20

<210> SEQ ID NO 11
<211> LENGTH: 19
<212> TYPE: DNA
<213> ORGANISM: Artificial Sequence
<220> FEATURE:
<223> OTHER INFORMATION: Primer

<400> SEQUENCE: 11
accacagtcc atgccatca                                                       19

<210> SEQ ID NO 12
<211> LENGTH: 20
<212> TYPE: DNA
<213> ORGANISM: Artificial Sequence
```

```
<220> FEATURE:
<223> OTHER INFORMATION: Primer

<400> SEQUENCE: 12
tccaccaccc tgttgctgta                                          20
```